United States Patent
Koo et al.

(10) Patent No.: US 6,806,229 B1
(45) Date of Patent: Oct. 19, 2004

(54) HERBICIDALLY ACTIVE PYRIDINE SULFONYL UREA DERIVATIVES

(75) Inventors: Suk-Jin Koo, Taejon (KR); Jin-Ho Cho, Taejon (KR); Jeong-Su Kim, Taejon (KR); Seung-Hun Kang, Taejon (KR); Kyung-Goo Kang, Taejon (KR); Dae-Whang Kim, Taejon (KR); Hae-Sung Chang, Taejon (KR); Young-Kwan Ko, Taejon (KR); Jae-Wook Ryoo, Taejon (KR)

(73) Assignee: LG Life Sciences, Seoul (KR)

( * ) Notice: Subject to any disclaimer, the term of this patent is extended or adjusted under 35 U.S.C. 154(b) by 22 days.

(21) Appl. No.: 10/089,625

(22) PCT Filed: Oct. 12, 2000

(86) PCT No.: PCT/KR00/01138

§ 371 (c)(1), (2), (4) Date: Jan. 8, 2003

(87) PCT Pub. No.: WO02/30921

PCT Pub. Date: Apr. 18, 2002

(51) Int. Cl.$^7$ .............. C07D 401/12; A01N 43/40
(52) U.S. Cl. ............... 504/215; 544/320; 544/331
(58) Field of Search ............ 504/215; 544/320, 544/331

(56) References Cited

FOREIGN PATENT DOCUMENTS

WO      WO 96/12708    * 5/1996

\* cited by examiner

*Primary Examiner*—Deepak Rao
(74) *Attorney, Agent, or Firm*—Peter F. Corless; John B. Alexander; Edwards & Angell, LLP

(57) ABSTRACT

The present invention relates to pyridine sulfonyl urea derivatives, salts or stereochemical isomers thereof showing an effective herbicidal activity in pre- and/or post-emergence treatment in rice farming, or to a method to use thereof, a method for the preparation thereof, an intermediate used for the preparation thereof, and a herbicidal composition comprising same.

10 Claims, No Drawings

HERBICIDALLY ACTIVE PYRIDINE SULFONYL UREA DERIVATIVES

TECHNICAL FIELD

The present invention relates to pyridine sulfonyl urea derivatives represented by the following formula (1):

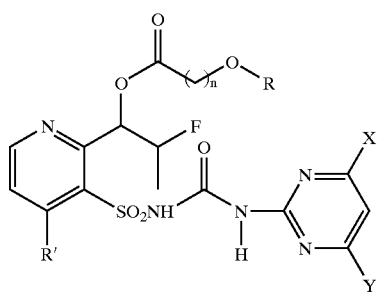
(1)

in which
n denotes an integer of from 1 to 3,
R represents H or $C_1$–$C_4$-alkyl,
R' represents H, $C_1$–$C_4$-alkyl, $C_1$–$C_3$-haloalkyl, halogen, or $C_1$–$C_2$-alkoxy, and
X and Y independently of one another represent $C_1$–$C_2$-alkyl, $C_1$–$C_2$-alkoxy, $C_1$–$C_2$-haloalkoxy, or halogen, salts or stereochemical isomers thereof showing an effective herbicidal activity in pre- and/or post-emergence treatment in rice farming, or to a method to use thereof, a method for the preparation thereof an intermediate used for the preparation thereof, and a herbicidal composition comprising same.

BACKGROUND ART

Hitherto, there have been reported a lot of sulfonyl urea derivatives having a herbicidal activity in rice farming. For example, JP 61/191602 discloses a compound represented by the following formula (2):

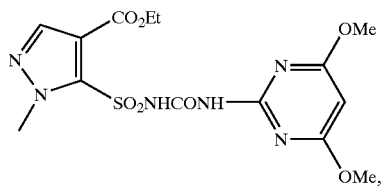
(2)

which has been commercialized as a herbicide for rice farming in the name of Pyrazosulfuron-ethyl.

Korean Patent No. 70675 discloses a compound represented by the following formula (3):

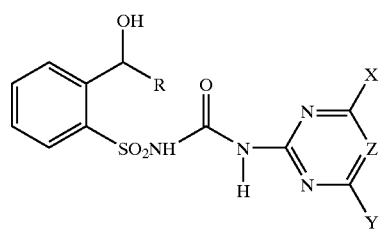
(3)

in which
R represents haloalkyl,
X and Y independently of one another represent $CH_3$, $OCH_3$, Cl, etc., and
Z represents CH or N.

Korean Patent Application No. 91-3014 discloses a herbicidally active sulfonyl urea derivative represented by the following formula (4):

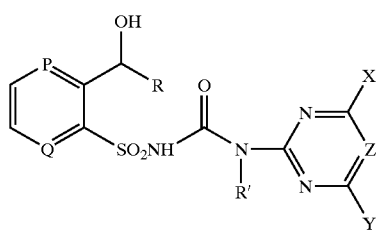
(4)

in which
R, X, Y and Z are defined as the above formula (3),
R' represents H or CH, and
P and Q independently of one another represent CH or N, but where the aromatic ring including P and Q is benzene or pyridine.

Korean Patent Application No. 93-6915 discloses a herbicidally active pyridine sulfonyl urea derivative represented by the following formula (5).

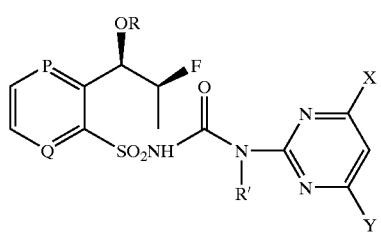
(5)

in which
P, Q, R', X and Y are defined as in the above formula (4),
R represents H, $R^a$—(C=O)— or $R^a$—$X^a$—(C=O)—, wherein $R^a$ represents $C_1$–$C_4$-alkyl, $C_1$–$C_3$-haloalkyl, $C_2$–$C_4$-alkenyl or $C_2$–$C_4$-alkynyl, and $X^a$ represents O, S, NH or $NR^a$.

The existing sulfonyl urea-based herbicidal compounds as explained above show an excellent herbicidal activity against annual and perennial weeds in rice, but have weak activity to barnyardgrass which is the most problematic weed in rice, or cause some phytotoxicity to rice plant. The present inventors claim new pyridine sulfonyl urea derivatives having improved rice safety and superior herbicidal activity against barnyardgrass to the earlier herbicidal compounds, and find great advantages of these new compounds when used as a rice herbicide.

Therefore, one object of the present invention is to provide the pyridine sulfonyl urea derivatives of the above formula (1), salts or stereochemical isomers thereof.

It is another object of the present invention is to provide a process for the preparation of the compound of formula (1).

It is further object of the present invention to provide a novel intermediate which is used for the preparation of the compound of formula (1).

It is further object of the present invention to provide a method to use the compound of formula (1) as a herbicide for paddy rice, and a herbicidal composition comprising same.

The present invention will be explained in more detail hereinafter.

DISCLOSURE OF INVENTION

The present invention relates to a compound of the following formula (1):

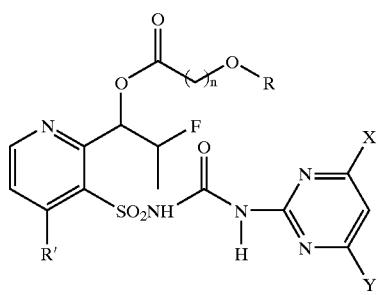

(1)

in which
n denotes an integer of from 1 to 3,
R represents H or $C_1$–$C_4$-alkyl,
R' represents H, $C_1$–$C_4$-alkyl, $C_1$–$C_3$-haloalkyl, halogen, or $C_1$–$C_2$-alkoxy, and
X and Y independently of one another represent $C_1$–$C_2$-alkyl, $C_1$–$C_2$-alkoxy, $C_1$–$C_2$-haloalkoxy, or halogen.

Among the compound of formula (1) which shows an excellent selectivity to rice plant and herbicidal activity to barnyardgrass and thus, can be advantageously used as a herbicide for rice farming, the preferred compounds include those wherein n denotes an integer of 1 or 2, R represents H or methyl, R' represents H, halogen or methyl, and X and Y each represents methoxy.

Particularly preferred compounds include those wherein n denotes an integer of 1 or 2, R represents methyl, R' represents H, Cl, Br or methyl, and X and Y each represents methoxy.

Typical examples of the compound of formula (1) according to the present invention are exemplified as follows:
N-[(4,6-dimethoxypyrimidin-2-yl)aminocarbonyl]-2-(2-fluoro-1-methoxyacetoxy-n-propyl)pyridine-3-sulfonamide.
N-[(4,6-dimethoxypyrimidin-2-yl)aminocarbonyl]-2-(2-fluoro-1-hydroxyacetoxy-n-propyl)pyridine-3-sulfonamide.
N-[(4,6-dimethoxypyrimidin-2-yl)aminocarbonyl]-2-(2-fluoro-1-(3-hydroxypropion)oxy-n-propyl)pyridine-3-sulfonamide.
N-[(4,6-dimethoxypyrimidin-2-yl)aminocarbonyl]-2-(2-fluoro-1-(3-methoxypropion)oxy-n-propyl)pyridine-3-sulfonamide.
N-[(4,6-dimethoxypyrimidin-2-yl)aminocarbonyl]-4-methyl-2-(2-fluoro-1-methoxyacetoxy-n-propyl)pyridine-3-sulfonamide.
N-[(4,6-dimethoxypyrimidin-2-yl)aminocarbonyl]-4-chloro-2-(2-fluoro-1-methoxyacetoxy-n-propyl)pyridine-3-sulfonamide.
N-[(4,6-dimethoxypyrimidin-2-yl)aminocarbonyl]-4-bromo-2-(2-fluoro-1-methoxyacetoxy-n-propyl)pyridine-3-sulfonamide.

Since the compound of formula (1) has two asymmetric carbons therein, they can exist as an erythro or threo isomer, or mixtures thereof. The compound of the present invention shows a stronger activity in the erythro form, but the mixtures thereof in a suitable mixing ratio also exhibit a sufficient activity.

The compound of formula (1) according to the present invention can be prepared by a process characterized in that a compound represented by the following formula (6):

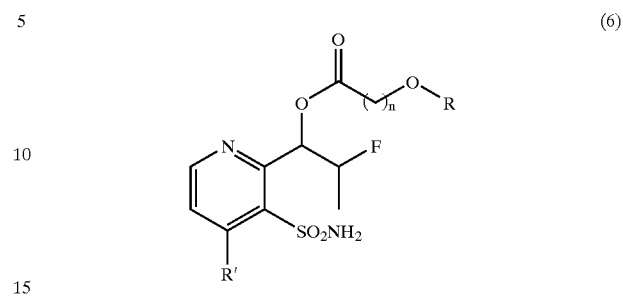

(6)

in which
n, R and R' are defined as in the above formula (1), is reacted in a solvent optionally in the presence of a base with a compound represented by the following formula (7):

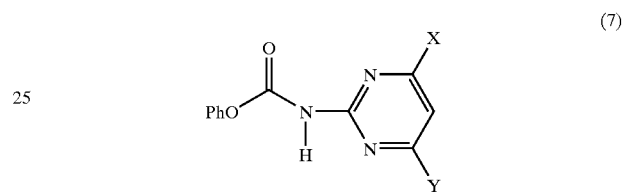

(7)

in which
X and Y are defined as in the above formula (1). Therefore, it is another object of the present invention to provide such a preparation process.

The compound of formula (6) used as a starting material in the process according to the present invention can exist as an erythro isomer, threo isomer, or mixtures thereof. The stereo-chemical configuration of the desired compound of formula (1) may be determined in line with the configuration of compound (6).

Any solvent which does not adversely affect the reaction can be used in the above process, but preferably tetrahydrofuran, acetone, acetonitrile, dioxane, methylene chloride, toluene, butanol, pyridine, dimethylformamide, etc. can be used. The above process is carried out preferably in the presence of a small amount of strong base, such as for example, triethylamine, hexamethylenetetramine, pyridine, DBU or DABCO (wherein DBU means 1,8-diazabicyclo[5,4,0]undec-7-ene and DABCO means 1,4-diazabicyclo[2,2,2]octane, and they have the same meaning throughout the present specification), etc., and the reaction temperature may be preferably maintained in the range of 10~80° C. The specific reaction conditions can be referred to U.S. Pat. No. 4,443,245 which discusses similar reactions, and after the reaction is completed, the desired compound can be obtained through the acid-treatment procedure as described in EP 044,807. If a highly pure compound is required, it is desirable to use HPLC technique.

The compound of formula (7) was known and can be easily prepared according to the process described in Korean Patent No. 70,675.

The compound of formula (6) is a novel intermediate which is provided first by the present invention. Therefore, it is another subject matter to be provided by the present invention. The compound of formula (6) can be prepared by treating a compound represented by the following formula (8):

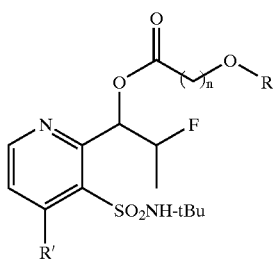

(8)

in which, n, R and R' are defined as formula (1), with trifluoroacetic acid (TFA) to eliminate the t-butyl group therefrom.

If the compound of formula (8) is stirred in the solvent of trifluoroacetic acid(TFA) at 0–80° C., the t-butyl group is eliminated to give the sulfonamide compound of formula (6). When the compound of formula (6) thus obtained is present in the form of an erythro-threo mixture, it may be resolved by column chromatography, HPLC or preparative-TLC method to give pure erythro or threo compound.

The compound of formula (8) may also be prepared by acylating a compound represented by the following formula (9) according to a conventional manner:

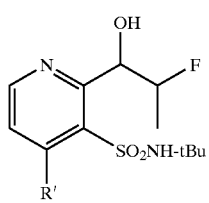

(9)

in which R' is defined as in the above formula (1).

The compound of formula (9) may be prepared by selectively reducing a compound represented by the following formula (10):

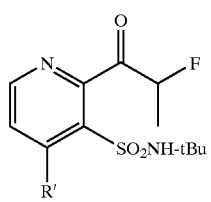

(10)

in which R' is defined as in the above formula (1), using a suitable reducing agent, such as for example, DIBAL.H(Diisobutylaluminum hydride), $NaBH_4$, $LiAlH_4$, $BH_3$.

The compound of formula (1) as can be prepared as explained above is more definitely exemplified individually in the following Table 1.

TABLE 1

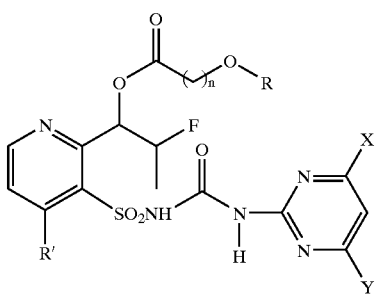

| R' | n | R | X | Y | m.p. (° C.) |
|---|---|---|---|---|---|
| Cl | 1 | $CH_3$ | Ome | OMe | 135–140 |
| Br | 1 | $CH_3$ | Ome | OMe | 87–89 |
| Br | 1 | H | Ome | OMe | |
| $OCH_3$ | 1 | $CH_3$ | Ome | OMe | |
| $CH_3$ | 1 | $CH_3$ | Ome | OMe | 156–158 |
| $CF_3$ | 1 | $CH_3$ | Ome | OMe | |
| H | 1 | H | Ome | OMe | 157–158 |
| $CH_3$ | 2 | $CH_3$ | Ome | OMe | |
| H | 1 | $CH_3$ | Ome | OMe | 175–177 (erythro) |
| H | 1 | $CH_3$ | Ome | OMe | 152–154 (threo) |
| H | 1 | $CH_3$ | Ome | Cl | |
| H | 1 | $CH_3$ | Me | Me | |
| H | 2 | H | Ome | OMe | 147–148 |
| H | 2 | $CH_3$ | Ome | OMe | 145–146 |

The compound of formula (1) according to the present invention may exist as a suitable salt and is utilizable as a herbicide in that form. The salt can be prepared by a conventional method known per se, for example, by contacting the compound of formula (1) with a solution containing hydroxide, alkoxide, or carbonate of alkali metal or alkaline earth metal. Otherwise, the salt may be prepared by using an amine compound in the similar manner.

Various salts can also be obtained by exchanging the cation of the salt of compound of formula (1) by another one. Cation exchange is carried out by directly contacting a salt of the compound of formula (1), for example, alkali metal salt or quarternary amine salt in aqueous solution with a solution containing the cation to be newly combined. This method is the most effective when the resulting salt containing the newly combined cation is insoluble in water. Ion exchange can also be carried out by subjecting a salt of the compound of formula (1), for example, alkali metal salt or quarternary amine salt in aqueous solution to a column filled with cation exchange resin containing the cation to be newly combined. In this case, the cation in the resin is exchanged with the cation of the original salt and the desired salt newly formed is eluted from the column. This method is particularly effective when the resulting salt is water-soluble, that is, sodium, potassium or calcium salt.

Further, the compound of formula (1) is conveniently used as a herbicidal agent when it is present in the form of mixtures or complexes with urea or amide compound. Those mixtures or complexes may be prepared according to the typical methods.

The preparation or conversion process as briefly summarized above may be easily carried out by a person skilled in the area of organic synthesis or synthesis of sulfonyl urea derivatives. All the processes designed from the present description by conventional modifications fall within the scope of the present invention.

As stated already, the pyridine sulfonyl urea derivative of formula (1) according to the present invention can be used as a herbicidal agent. Therefore, the utilities and formulations are explained below.

[Utility]

Since the compound of formula (1) has an excellent selectivity for rice plant as well as a potent herbicidal activity, it can be used as a herbicide for paddy rice and can be contained as an active ingredient in herbicidal composition.

Test results indicate that the compound of formula (1) is highly active as a herbicide for pre- or post-emergence treatment in paddy and upland.

The rates of application of the active compound of the invention are determined by a number of factors, including the types of weeds to be controlled, weather, climate, formulations selected, mode of application, size of weeds, etc. In general terms, the subject compounds should be applied at levels of around 1 g to 1 kg/ha, the lower rates being suggested for use on soils having a low organic matter content or sandy soil, for young plants, or for situations where only short-term persistence is required. Particularly, the subject compounds may be used effectively in rice to control various weeds including barnyardgrass, annual broadleaf and sedge weeds as well as perennial weeds.

The compounds of the present invention may be used alone or as two-, three-, or four-way combinations together with the existing herbicides.

[Formulation]

In the present invention, the compound of formula (1) is used in the form of a conventional composition. If necessary, the compound of formula (1) is applied to plant, soil, or water surface in combination with carriers, surfactants, adjuvants, or other additives which are conveniently used in the technical field of formulation Suitable carriers and additives may be a solid or a liquid and include those components effectively used in the field of formulation, such as for example, natural or synthetic inorganic substances, solvents, dispersants, wetting agents, adhesive agents, thickening agents, binding agents, etc.

The composition comprising the compound of formula (1) is preferably applied to soil in the form of a solid, for example, a granule, or liquid (soil treatment). Otherwise, the composition comprising the compound of formula (1) may be applied directly to a plant foliage (foliar treatment). Frequency and rate of application are varied depending on the biological characteristics of plants, weather, soil types, and other environmental conditions.

The active ingredient-containing combinations in unmodified form can be used together with the known adjuvants conveniently used in the field of formulation. They are formulated according to the known methods to emulsifiable concentrates, liquid formulations which can be diluted, liquid hydrates which can be directly applied to water surface, developing agent for water surface, emulsions, hydrates, powders, dusts, granules or tablets. Application methods such as spraying, dusting, broadcasting, etc. and characteristics of the composition are selected to be compatible with the purpose of use and environments. The rate of application of the active ingredient-containing combination varies generally in the range of from 1 g to 1 kg a.i./ha, preferably from 10 g to 30 g a.i./ha.

For example, the active ingredient may be intimately mixed and/or pulverized with extenders[e.g. solvents, solid carriers and if desired, surface-active compounds (surfactants)] according to the known methods to give the combinations.

Possible solvents include the following: aromatic hydrocarbons such as xylene mixtures or substituted naphthalenes; alcohols and glycols, and their ethers and esters such as ethanol, ethylene glycol ethylene glycol monomethyl or monoethyl ether; ketones such as cyclohexanone; strongly polar solvents such as N-methyl-2-pyrrolidone, dimethylsulfoxide or dimethylformamide; optionally epoxidised vegetable oils such as epoxidised coconut oil or soybean oil; and water. These solvents can be used as emulsifying agents, solvents for liquid formulation or cosolvents for granule formulation.

The solid carriers used e.g. for dusts and granules, are normally pulverized natural mineral fillers such as talc, kaolin, montmorillonite, pyrophyllite, bentonite, calcite, or adsorptive carriers such as zeolite, or sand. In addition, a great number of prepulverized materials of inorganic or organic nature can be used.

Depending on the nature of the compound of formula (1) to be formulated, suitable surface-active compounds are nonionic, cationic and/or anionic surfactants having good dispersing, wetting and lubricating properties. The term "surfactants" will also be understood as comprising mixtures of surfactants.

The herbicidal compositions, broadly, contain 0.1 to 99% by weight, preferably 0.1 to 95% by weight of the compound of formula (1), 99.9 to 1% by weight, preferably 99.9 to 5% by weight of solid or liquid additives, and 0 to 25% by weight, preferably 0.1 to 25% by weight of surfactant.

These compositions fall within the scope of the present invention.

BEST MODE FOR CARRYING OUT THE INVENTION

The process for the preparation and use of the compound according to the present invention will be more specifically explained in the following Examples. However, it should be understood that these Examples are intended to illustrate the present invention but not in any manner to limit the scope of the present invention. Unless otherwise stated, C18 silica (25–40 μm, 50 ml) column equilibrated with acetonitrile/water=10/90(v/v) was used as the stationary phase of column chromatography in the following Examples.

EXAMPLE 1

Synthesis of erythro-N-t-butyl-4-methyl-2-(2-fluoro-1-hydroxy-n-propyl)pyridine-3-sulfonamide Erythro-N-t-butyl-2-(2-fluoro-1-hydroxy-n-propyl)pyridine-3-sulfonamide (2.55 g) was dissolved in THF(150 ml) which had been well purified and then 2.5N n-BuLi(13.4 ml) was slowly added thereto under nitrogen gas at −78° C. The reaction temperature was raised to −20° C. and cooled down to −78° C. again. CuI(2.10 g) was introduced into another flask and the lithium salt prepared above was reversely added to this flask. After 10 minutes, $CH_3I$(0.83 ml) was added, the resulting mixture was stirred for 30 minutes at −78° C., and the reaction was quenched with $NH_4Cl$ solution. Ethyl acetate was added to the reaction solution to separate the organic layer. The aqueous layer was extracted with ethyl acetate, and then the organic layers were combined, dried($MgSO_4$), filtered and concentrated to give a crude product. This crude product was subjected to column chromatography (Moving phase: ethyl acetate/n-hexane=1/2, v/v) to give 0.5 g of the pure title compound.

$^1$H NMR(200 MHz, $CDCl_3$): δ 8.55 (d, 1H, J=5 Hz), 7.24 (d, 1H, J=5 Hz), 6.1 (br s, 1H), 4.6~4.9 (m, 3H), 2.76 (s, 3H), 1.35 (dd, 3H, $J_1$=25 Hz, $J_2$=6 Hz), 1.25 (s, 9H).

EXAMPLE 2

Synthesis of erythro-4-methyl-2-(2-fluoro-1-methoxy-acetoxy-n-propyl)pyridine-3-sulfonamide Erythro-N-t-butyl-4-methyl-2-(2-fluoro-1-hydroxy-n-propyl)pyridine-3-sulfonamide(0.7 g) was dissolved in THF (10 ml) and methoxyacetylchloride(0.32 g) was added thereto. 60% NAH(0.13 g) was added at 0° C. and the resulting mixture was stirred for 2 hours at room temperature. The reaction was quenched with saturated aqueous $NH_4Cl$ solution and extracted with ethyl acetate. The organic layer was dried($MgSO_4$), filtered and concentrated, and the residue was subjected to column chromatography (Moving phase: ethyl acetate/n-hexane=1/3, v/v) to give erythro-N-t-butyl-4-methyl-2-(2-fluoro-1-methoxyacetoxy-n-propyl)pyridine-3-sulfonamide(0.7 g).

To the resulting product was added $CF_3CO_2H$(10 ml) and the mixture was stirred for 1 hour at 60~65° C. The reaction solution was concentrated under reduced pressure and the residue was dissolved in methylene chloride and washed with aqueous sodium bicarbonate solution. The organic layer was dried($MSO_4$), and concentrated, and the residue was subjected to column chromatography (Moving phase: ethyl acetate/methylene chloride=1/7→1/1, v/v) to give 0.37 g of the pure title compound.

$^1$H NMR(200 MHz, $CDCl_3$): δ 8.57 (d, 1H, J=5 Hz), 7.24 (d, 1H, J=5 Hz), 6.85~6.95 (m, 1H), 5.65 (br s, 2H), 4.9~5.3 (m, 1H), 4.13 (s, 2H), 3.41 (s, 2H), 2.72 (s, 3H), 1.55 (dd, 3H, $J_1$=25 Hz, $J_2$=6 Hz).

EXAMPLE 3

Synthesis of erythro-N-t-butyl-4-chloro-2-(2-fluoro-1-hydroxy-n-propyl)pyridine-3-sulfonamide Erythro-N-t-butyl-2-(2-fluoro-1-hydroxy-n-propyl)pyridine-3-sulfonamide(0.29 g) was dissolved in THF(10 ml) which had been well purified and then 2.5N n-BuLi(1.52 ml) was slowly added thereto under nitrogen gas at −78° C. The reaction temperature was raised to −20° C. and cooled down to −78° C. again. NCS(N-chlorosuccinimide)(0.2 g) dissolved in THF(5 ml) was slowly added to the reaction solution. After 30 minutes, the reaction was quenched with saturated aqueous ammonium chloride solution. Ethyl acetate was added to the reaction solution to separate the organic layer. The aqueous layer was extracted once more with ethyl acetate, and then the organic layers were combined, dried ($MgSO_4$), filtered and concentrated to give a crude product. This crude product was subjected to column chromatography (Moving phase: ethyl acetate/n-hexane=1/2, v/v) to give 0.18 g of the pure title compound.

$^1$H NMR(200 MHz, $CDCl_3$): δ 8.61 (d, 1H, J=5 Hz), 7.50 (d, 1H, J=5 Hz), 6.05~6.15 (br s, 1H), 5.2 (br s, 1H), 4.6~4.9 (m, 2H), 1.35 (dd, 3H, $J_1$=25 Hz, $J_2$=6 Hz), 1.25 (s, 9H).

EXAMPLE 4

Synthesis of erythro-N-t-butyl-chloro-2-(2-fluoro-1-methoxyacetoxy-n-propyl)pyridine-3-sulfonamide Erythro-N-t-butyl-4-chloro-2-(2-fluoro-1-hydroxy-n-propyl)pyridine-3-sulfonamide(0.75 g) was dissolved in THF(10 ml) and methoxyacetylchloride(0.33 g) was added thereto. The reaction solution was cooled down to 0° C. and 60% NaH (0.13 g) was added. The resulting solution was warmed to room temperature and stirred for 2 hours. The reaction was quenched with aqueous ammonium chloride solution. The reaction solution was extracted with ethyl acetate and the organic layer was dried ($MgSO_4$), filtered and concentrated. The residue was subjected to column chromatography (Moving phase: ethyl acetate/n-hexane=1/3, v/v) to give 0.7 g of the pure title compound.

$^1$H NMR(200 MHz, $CDCl_3$): δ 8.60 (d, 1H, J=5 Hz), 7.46 (d, 1H, J=5 Hz), 7.05~7.15 (m, 1H), 5.45 (br s, 1H), 4.9~5.3 (m, 1H), 2.1 (s, 3H), 1.44 (dd, 3H, $J_1$=25 Hz, $J_2$=6 Hz), 1.31 (s, 9H).

EXAMPLE 5

Synthesis of erythro-N-t-butyl-4-bromo-2-(2-fluoro-1-hydroxy-n-propyl)pyridine-(3-sulfonamide Erythro-N-t-butyl-2-2-fluoro-1-hydroxy-n-propyl)pyridine-3-sulfonamide(7.0 g) was dissolved in THF(200 ml) which had been well purified and then 2.5N n-BuLi (13.4 ml) was slowly added thereto under nitrogen gas at −78° C. The reaction temperature was raised to −20° C. and cooled down to −78° C. again. NBS(N-bromosuccinimide) (6.4 g) was added to the reaction solution and the resulting mixture was stirred for 30 minutes. The reaction was quenched with saturated aqueous ammonium chloride solution. Ethyl acetate was added to the reaction solution to separate the organic layer. The aqueous layer was extracted once more with ethyl acetate, and then the organic layers were combined, dried ($MgSO_4$), filtered and concentrated to give a crude product. This crude product was subjected to column chromatography (Moving phase: ethyl acetate/n-hexane=1/2, v/v) to give 3.9 g of the pure title compound.

$^1$H NMR(200 MHz, $CDCl_3$): δ 8.48 (d, 1H, J=5 Hz), 7.74 (d, 1H, J=5 Hz), 6.5 (br s, 1H), 5.39 (br s, 1H), 4.6~4.95 (m, 2H), 1.32 (dd, 3H, $J_1$=25 Hz, $J_2$=6 Hz), 1.25 (s, 9H).

EXAMPLE 6

Synthesis of erythro-4-bromo-2-(2-fluoro-1-hydroxy-n-propyl)pyridine-3-sulfonamide Erythro-N-t-butyl-4-bromo-2-(2-fluoro-1-hydroxy-n-propyl)pyridine-3-sulfonamide(0.5 g) was dissolved in trifluoroacetic acid($CF_3CO_2H$; 10 ml) and the resulting solution was stirred for 2 hours at 60~65° C. The reaction solution was concentrated under reduced pressure, and then the filtrate was diluted with methylene chloride and concentrated. The residue was subjected to column chromatography (Moving phase: ethyl acetate/methylene chloride=1/7→1/1, v/v) to give 0.3 g of the pure title compound.

$^1$H NMR(200 MHz, $CDCl_3$): δ 8.49 (d, 1H, J=5 Hz), 7.75 (d, 1H, J=5 Hz), 6.0~6.06 (m, 1H), 5.45 (br s, 2H), 4.15~4.55(m, 1H), 3.46 (br s, 1H), 1.53 (dd, 3H, $J_1$=25 Hz, $J_2$=6 Hz).

EXAMPLE 7

Synthesis of erythro-N-[(4,6-dimethoxypyrimidin-2-yl)aminocarbonyl]-4-chloro-2-(2-fluoro-1-methoxyacetoxy-n-propyl)pyridine-3-sulfonamide Erythro-4-chloro-2-(2-fluoro-1-methoxyacetoxy-n-propyl)pyridine-3-sulfonamide (0.5 g) was dissolved in acetonitrile(10 ml) and phenyl (4,6-dimethoxypyrimidin-2-yl)carbamate(0.86 g) was added thereto at room temperature. DBU(0.48 g) was slowly added and the reaction solution was stirred for 30 minutes, diluted with methylene chloride(100 ml) and washed with 5% aqueous hydrochloric acid solution(50 ml). The organic layer was dried ($MgSO_4$), filtered and concentrated. The residue was recrystallized from diethylether/n-hexane to give 0.61 g of the pure title compound as a white solid.

m.p.: 135~140° C.

$^1$H NMR(200 MHz, $CDCl_3$): δ 13.2 (br s, 1H), 8.63 (d, 1H, J=5 Hz), 7.45 (d, 1H, J=5 Hz), 7.2~7.4 (m, 2H), 5.81 (s, 1H), 4.82~5.22 (m, 1H), 3.97 (s, 6H), 1.44 (dd, 3H, $J_1$=25 Hz, $J_2$=6 Hz).

EXAMPLE 8

Synthesis of erythro-N-[(4,6-dimethoxypyrimidin-2-yl)aminocarbonyl]-4-bromo-2-(2-fluoro-1-methoxyacetoxy-n-propyl)pyridine-3-sulfonamide Erythro-4-bromo-2-(2-fluoro-1-methoxyacetoxy-n-propyl)pyridine-3-sulfonamide (0.82 g) and phenyl (4,6- dimethoxypyrimidin-2-yl)carbamate(0.86 g) were reacted according to the same procedure as Example 7 to give 0.85 g of the title compound as a white solid.

m.p.: 87–89° C.

$^1$H NMR(200 MHz CDCl$_3$) δ 8.49 (d, 1H, J=5 Hz), 7.65 (d, 1H, J=5 Hz), 7.23 (s, 1H), 7.02–7.1 (m, 1H), 5.80 (s, 1H), 5.22–5.58 (m, 1H), 4.13 (s, 2H), 3.96 (s, 6H), 3.41 (s, 3H), 1.48 (dd, 3H, J$_1$=25 Hz, J$_2$=6 Hz).

EXAMPLE 9

Synthesis of erythro-N-[(4,6-dimethoxypyrimidin-2-yl)aminocarbonyl]-4-methyl-2-(2-fluoro-1-methoxyacetoxy-n-propyl)pyridine-3-sulfonamide Erythro-4-methyl-2-(2-fluoro-1-methoxyacetoxy-n-propyl)pyridine-3-sulfonamide (0.73 g) and phenyl (4,6-dimethoxypyrimidin-2-yl)carbamate(0.86 g) were reacted according to the same procedure as Example 7 to give 0.75 g of the title compound as a white solid.

m.p.: 156–158° C.

$^1$H NMR(200 MHz, CDCl$_3$) δ 8.58 (d, 1H, J=5 Hz), 7.23 (d, 1H, J=5 Hz), 7.21 (br s, 1H), 6.65–6.75 (m, 1H), 5.78 (s, 1H), 5.05–5.38 (m, 1H), 4.13 (s, 2H), 3.97 (s, 6H), 3.41 (s, 3H), 2.89 (s, 3H), 1.47 (dd, 3H, J$_1$=25 Hz, J$_2$=6 Hz).

EXAMPLE 10

Synthesis of erythro-2-(2-fluoro-1-methoxyacetoxy-n-propyl)pyridine-3-sulfonamide and threo-2-(2-fluoro-1-methoxyacetoxy-n-propyl)pyridine-3-sulfonamide 1:1 mixture of erythro and threo isomers of N-t-butyl-2-(2-fluoro-1-methoxyacetoxy-n-propyl)pyridine-3-sulfonamide(5.0 g) was dissolved in trifluoroacetic acid(20 ml). The reaction solution was stirred for 12 hours at 45° C. and concentrated under reduced pressure. The residue was dissolved in methylene chloride, which was then washed with aqueous sodium bicarbonate solution. The organic layer was dried over anhydrous magnesium sulfate and the residue was subjected to column chromatography (Moving phase: ethyl acetate/methylene chloride=1/7→1/1, v/v) to give 1.0 g of the title compound in the pure erythro form and 1.0 g of the title compound in the pure threo form, respectively, as a solid.

Erythro compound.

$^1$H NMR(200 MHz, CDCl$_3$): δ 8.82–8.85 (m, 1H), 8.35–8.38 (m, 1H), 7.43–7.50 (m, 1H), 6.60–6.72 (m, 1H), 5.68 (brs, 2H), 4.93–5.29 (m, 1H), 4.18 (s, 2H), 3.2 (s, 3H), 1.55 (dd, 3H, J$_{H-H}$=6.5 Hz, J$_{H-F}$=25 Hz).

Threo compound $^1$H NMR(270 MHz, CDCl$_3$): δ 8.82–8.85 (m, 1H), 8.35–8.38 (m, 1H), 7.43–7.50 (m, 1H), 6.60–6.72 (m, 1H), 5.58 (brs, 2H), 5.29–5.40 (m, 1H), 4.18 (s, 2H), 3.43 (s, 3H), 1.20 (dd, 3H, J$_{H-H}$=6.5 Hz, J$_{H-F}$=25 Hz).

EXAMPLE 11

Synthesis of erythro-2-(2-fluoro-1-hydroxyacetoxy-n-propyl)pyridine-3-sulfonamide Erythro-2-(2-fluoro-1-methoxyacetoxy-n-propyl)pyridine-3-sulfonamide(0.5 g) was dissolved in chloroform (10 ml), iodotrimethylsilane(0.9 ml) was added thereto, and the resulting mixture was stirred for 12 hours at 60° C. The reaction solution was concentrated and the residue was subjected to C18 silica(50 ml) column chromatography (Moving phase: CH$_3$CN/H$_2$O=10/90, v/v) to give 0.22 g of the title compound.

m.p.: 142–143° C.

$^1$H NMR(200 MHz, D$_2$O): δ 8.82–8.85 (m, 1H), 8.35–8.38 (m, 1H), 7.43–7.50 (m, 1H), 5.0–5.4 (m, 1H), 4.4 (d, 2H), 1.55 (dd, 3H).

EXAMPLE 12

Synthesis of erythro-2-(2-fluoro-1-(3-methoxypropion)oxy-n-propyl)pyridine-3-sulfonamide Erythro-N-t-butyl-2-(2-fluoro-1-(3-methoxypropion)oxy-n-propyl)pyridine-3-sulfonamide(5.0 g) was reacted according to the same procedure as Example 10 to give 2.0 g of the title compound.

$^1$H NMR(200 MHz, CDCl$_3$): δ 8.82–8.85 (m, 1H), 8.35–8.38 (m, 1H), 7.43–7.50 (m, 1H), 6.60–6.72 (m, 1H), 5.75 (brs, 2H), 4.93–5.29 (m, 1H), 3.62(t, 2H), 3.3 (s, 3H), 2.7 (m, 2H), 1.55 (dd, 3H).

EXAMPLE 13

Synthesis of erythro-2-(2-fluoro-1-(3-hydroxypropion)oxy-n-propyl)pyridine-3sulfonamide Erythro-2-(2-fluoro-1-(3-methoxypropion)oxy-n-propyl)pyridine-3-sulfonamide (0.56 g) was reacted according to the same procedure as Example 11 to give 0.12 g of the title compound.

$^1$H NMR(200 MHz, D$_2$O): δ 8.8 (m, 1H), 8.4 (m, 1H), 7.45 (m, 1H), 6.9 (brs, 2H), 6.75 (m, 1H), 5.0–5.3 (m, 1H), 3.8 (m, 2H), 2.6 (t, 2H), 1.55 (dd, 3H).

EXAMPLE 14

Synthesis of erythro-N-[-(4,6-dimethoxypyrimidin-2-yl)aminocarbonyl]-2-(2-fluoro-1-methoxyacetoxy-n-propyl)pyridine-3-sulfonamide Erythro-2-(2-fluoro-1-methoxyacetoxy-n-propyl)pyridine-3-sulfonamide(3.9 g) was dissolved in acetonitrile (20 ml), phenyl (4,6-dimethoxypyrimidin-2-yl)carbamate (3.57 g)was added, and then triethylamine(1.32 g) was slowly added thereto. The reaction solution was stirred for 2 hours, diluted with methylene chloride(20 ml) and then washed with 5% aqueous hydrochloric acid solution(10 ml) and water(10 ml). The organic layer was dried over magnesium sulfate, filtered and concentrated. The residue was recrystallized from ethyl acetate/hexane/diethylether to give 4.5 g of the title compound.

m.p.: 175–177° C.

$^1$H NMR(200 MHz, CDCl$_3$): δ 13.2 (br, 1H), 8.8 (m, 1H), 8.6 (m, 1H), 7.5 (m, 1H), 7.2 (br, 1H), 6.6 (m, 1H), 5.80 (s, 1H), 5.0–5.3 (m, 1H), 4.05 (s, 2H), 3.96 (s, 6H), 3.25 (s, 3H), 1.45 (dd, 3H).

EXAMPLE 15

Synthesis of threo-N-[(4,6-dimethoxypyrimidin-2-yl)aminocarbonyl]-2-(2-fluoro-1-methoxyacetoxy-n-propyl)pyridine-3-sulfonamide Threo-2-(2-fluoro-1-methoxyacetoxy-n-propyl)pyridine-3-sulfonamide (1.56 g) and phenyl (4,6-dimethoxypyrimidin-2-yl)carbamate(2.99 g) were reacted according to the same procedure as Example 14 to give 1.8 g of the title compound as a white solid.

m.p.: 152–154° C.

$^1$H NMR(200 MHz, CDCl$_3$): δ 13.2 (br, 1H), 8.81 (m, 1H), 8.67 (m, 1H), 7.50 (m, 1H), 7.49 (br, 1H), 6.67 (m, 1H), 5.80 (s, 1H), 5.0–5.3(m, 1H), 4.05 (s, 2H), 3.96 (s, 6H), 3.25 (s, 3H), 1.28 (dd, 3H).

EXAMPLE 16

Synthesis of erythro-N-[(4,6-dimethoxypyrimidin-2-yl)aminocarbonyl]-2-(2-fluoro-1-hydroxyacetoxy-n-propyl)pyridine-3-sulfonamide Erythro-2-(2-fluoro-1-hydroxyacetoxy-n-propyl)pyridine-3-sulfonamide(1.2 g) and phenyl (4,6-dimethoxypyrimidin-2-yl)carbamate(1.33 g) were reacted according to the same procedure as Example 14 to give 1.5 g of the title compound as a white solid.

m.p.: 157–158° C.

$^1$H NMR(200 MHz, CDCl$_3$): δ 8.8 (m, 1H), 8.05 (m, 1H), 7.5 (m, 1H), 6.7–6.8 (m, 1H), 5.80 (s, 1H), 5.0–5.3 (m, 1H), 4.2 (m, 2H), 3.95 (s, 6H), 1.45 (dd, 3H).

EXAMPLE 17

Synthesis of erythro-N-[(4,6-dimethoxypyrimidin-2-yl)aminocarbonyl]-2-(2-fluoro-1-(3-hydroxypropion)oxy-n-propyl)pyridine-3-sulfonamide Erythro-2-(2-fluoro-1-(3-hydroxypropion)oxy-n-propyl)pyridine-3-sulfonamide (0.11 g) and phenyl (4,6-dimethoxypyrimidin-2-yl)carbamate(0.18 g) were reacted according to the same procedure as Example 14 to give 0.13 g of the title compound.

m.p.: 147–148° C.

$^1$H NMR(200 MHz, CDCl$_3$): δ 13.3 (br, 1H), 8.8 (m, 1H), 8.65 (m, 1H), 7.6 (m, 1H), 7.3 (br, 1H), 5.80 (s, 1H), 5.0–5.3 (m, 1H), 3.96 (s, 6H), 3.6–3.9 (m, 2H), 3.4 (br, 1H), 2.6 (m, 2H), 1.45 (dd, 3H).

EXAMPLE 18

Synthesis of erythro-N-[(4,6-dimethoxypyrimidin-2-yl)aminocarbonyl]-2-(2-fluoro-1-(3-methoxypropion)oxy-n-propyl)pyridine-3-sulfonamide Erythro-2-(2-fluoro-1-(3-methoxypropion)oxy-n-propyl)pyridine-3-sulfonamide (0.29 g) and phenyl (4,6-dimethoxypyrimidin-2-yl)carbamate(0.53 g) were reacted according to the same procedure as Example 14 to give 0.35 g of the title compound.

m.p.: 145–146° C.

$^1$H NMR(200 MHz, CDCl$_3$): δ 8.8 (m, 1H), 8.6 (m, 1H), 7.5 (m, 1H), 7.2 (br, 1H), 6.6 (m, 1H), 5.80 (s, 1H), 4.95–5.25 (m, 1H), 3.95 (s, 6H), 3.45 (t, 2H), 3.2 (s, 3H), 2.5 (m, 2H), 1.5 (dd, 3H).

EXAMPLE 19

Herbicidal activities of the compounds according to the present invention and the known standard compounds as represented in the following Table 2 were estimated in a greenhouse.

TABLE 2

| Compound of the present invention | Structure | Standard Compound | Structure |
|---|---|---|---|
| 1 | (structure) | A | (structure) |
| 2 | (structure) | B | (structure) |

TABLE 2-continued

| Compound of the present invention | Structure | Standard Compound | Structure |
|---|---|---|---|
| 3 | (pyridine with CH(OC(O)CH2CH2OH)-CHFMe substituent, and SO2NHCONH-(4,6-dimethoxypyrimidin-2-yl)) | C | (pyridine with CH(OH)-CHFMe substituent, and SO2NHCONH-(4,6-dimethoxypyrimidin-2-yl)) |
| 4 | (pyridine with CH(OC(O)CH2CH2OMe)-CHFMe substituent, and SO2NHCONH-(4,6-dimethoxypyrimidin-2-yl)) | D | (pyridine with CH(OC(O)Me)-CHFMe substituent, and SO2NHCONH-(4,6-dimethoxypyrimidin-2-yl)) |
| 5 | (4-chloro pyridine with CH(OC(O)CH2OMe)-CHFMe substituent, and SO2NHCONH-(4,6-dimethoxypyrimidin-2-yl)) | E | (1-methylpyrazole-4-carboxylic acid ethyl ester with 5-SO2NHCONH-(4,6-dimethoxypyrimidin-2-yl)) |
| 6 | (4-bromo pyridine with CH(OC(O)CH2OMe)-CHFMe substituent, and SO2NHCONH-(4,6-dimethoxypyrimidin-2-yl)) | | |
| 7 | (4-methyl pyridine with CH(OC(O)CH2OMe)-CHFMe substituent, and SO2NHCONH-(4,6-dimethoxypyrimidin-2-yl)) | | |

Test for Herbicidal Activity and Phytotoxicity in Paddy Field

Pots having a surface area of 150 cm² were filled with a small amount of fertilizer and sterilized paddy field soil in a muddy state with a depth of 5 cm. Five (5) seeds of pre-germinated rice were directly sown on the soil surface and three (3) rice seedlings (2~3 leaves) prepared in advance were transplanted in a depth of 2 cm in each pot. In another pot, seeds of barnyardgrass were sown and incorporated into the surface layer of soil. After sowing and transplanting of rice plant and sowing of barnyardgrass, the pots were flooded with water 3 cm deep and kept in a greenhouse. The rice plant was treated with the chemicals 5 days after sowing or transplanting, and barnyardgrass was treated with the chemicals at the pre-emergence (5 days after from sowing) and post-emergence stage (at the three-leaf stage, usually after 15 days from sowing).

Suitable herbicidal compositions were prepared by mixing and dissolving 1 part by weight of the active compound with 5 parts by weight of acetone and 1 part by weight of alkylaryl polyglycolether as an emulsifier and then diluting with water to the predetermined concentration. Application was made by dropping the herbicide solutions onto the water surface of the pots.

The test plants were observed for two weeks after the treatment with the chemicals and then herbicidal activity and phytotoxicity of the test compounds were visually rated in a percent (%) scale, where 0 means no activity or phytotoxicity and 100 means complete death.

The herbicidal activity and phytotoxicity in paddy field of the compound of formula (1) and the known standard compounds are given in the following Tables 3a and 3b, respectively.

Among the compounds, the standard compound E is Pyrazosulfuron-ethyl, which is the most widely used herbicide in rice at the present time. The standard compounds A, B, C and D have similar structure to the compound of formula (1) of the present invention, and were filed already.

TABLE 3a

Herbicidal activity and phytotoxicity of the standard compounds in a paddy condition.

| Standard Compound | Rate (g/ha) | Oryza sativa | | Echinochloa crus-galli | | |
|---|---|---|---|---|---|---|
| | | Seed | Transplanted | Rate (g/ha) | Pre-emergence | Post-emergence (3-Leaf stage) |
| A | 80 | 80 | 70 | 30 | 100 | 100 |
| | 40 | 50 | 40 | 20 | 100 | 95 |
| | 20 | 40 | 30 | 10 | 100 | 90 |
| | 10 | 40 | 20 | 5 | 60 | 60 |
| B | 80 | 70 | 60 | 30 | 100 | 100 |
| | 40 | 50 | 40 | 20 | 100 | 90 |
| | 20 | 40 | 20 | 10 | 100 | 90 |
| | 10 | 30 | 20 | 5 | 50 | 50 |
| C | 80 | 70 | 50 | 30 | 100 | 100 |
| | 40 | 30 | 30 | 20 | 100 | 100 |
| | 20 | 20 | 20 | 10 | 100 | 90 |
| | 10 | 10 | 10 | 5 | 40 | 60 |
| D | 80 | 60 | 50 | 30 | 100 | 100 |
| | 40 | 30 | 20 | 20 | 100 | 100 |
| | 20 | 20 | 10 | 10 | 100 | 90 |
| | 10 | 10 | 0 | 5 | 30 | 50 |
| E (Pyrazo-sulfuron-ethyl) | 80 | 30 | 10 | 30 | 30 | 20 |
| | 40 | 20 | 0 | 20 | 20 | 0 |
| | 20 | 10 | 0 | 10 | 10 | 0 |
| | 10 | 0 | 0 | 5 | 0 | 0 |

As shown in Table 3a, the standard compound E, at 80 g/ha which is the four-times higher rate than the conventional application rate (20 g/ha), shows little phytotoxicity to rice; 10 or 30% to the transplanted or direct-seeded rice, respectively. Therefore, the compound E is considered to be highly safe to rice. However, it shows weak herbicidal activity to barnyardgrass (10% at 20 g/ha), which is the most important weed in rice.

On the contrary, the standard compounds A to D show excellent activity to barnyardgrass, i.e., 95% or greater activity at 20 g/ha by pre- or post-emergence treatments. These compounds (A~D) also show rice safety at 20 g/ha; 10 to 40% of phytotoxicity depending on the compounds. However, for commercial development, a compound should be safe at four-times higher rates than the recommended rate. The compounds A~D show 50~80% of phytotoxicity depending on the compounds at 80 g/ha, which is four times as much as the typical dose, and thus, are considered to be impossible to develop commercially.

TABLE 3b

Herbicidal activity and phytotoxicity of the compounds of the present invention in a paddy condition.

| Compound | Rate (g/ha) | Oryza sativa | | Echinochloa crus-galli | | |
|---|---|---|---|---|---|---|
| | | Seed | Transplanted | Rate (g/ha) | Pre-emergence | Post-emergence (3-Leaf stage) |
| Com. 1 | 80 | 30 | 20 | 30 | 90 | 100 |
| | 40 | 30 | 10 | 20 | 90 | 90 |
| | 20 | 10 | 10 | 10 | 80 | 80 |
| | 10 | 0 | 0 | 5 | 50 | 60 |
| Com. 2 | 80 | 30 | 10 | 30 | 100 | 100 |
| | 40 | 20 | 10 | 20 | 100 | 100 |
| | 20 | 0 | 0 | 10 | 100 | 90 |
| | 10 | 0 | 0 | 5 | 60 | 50 |
| Com. 3 | 80 | 30 | 20 | 30 | 100 | 100 |
| | 40 | 30 | 20 | 20 | 95 | 90 |
| | 20 | 10 | 10 | 10 | 90 | 80 |
| | 10 | 0 | 5 | 5 | 60 | 60 |
| Com. 4 | 80 | 30 | 20 | 30 | 100 | 100 |
| | 40 | 20 | 10 | 20 | 100 | 100 |
| | 20 | 0 | 0 | 10 | 95 | 90 |
| | 10 | 0 | 0 | 5 | 60 | 60 |
| Com. 5 | 80 | 30 | 20 | 30 | 100 | 100 |
| | 40 | 20 | 0 | 20 | 90 | 90 |
| | 20 | 10 | 0 | 10 | 80 | 70 |
| | 10 | 0 | 0 | 5 | 50 | 60 |
| Com. 6 | 80 | 20 | 20 | 30 | 100 | 100 |
| | 40 | 10 | 0 | 20 | 100 | 90 |
| | 20 | 0 | 0 | 10 | 80 | 70 |
| | 10 | 0 | 0 | 5 | 60 | 50 |
| Com. 7 | 80 | 30 | 20 | 30 | 100 | 100 |
| | 40 | 20 | 10 | 20 | 90 | 95 |
| | 20 | 0 | 0 | 10 | 80 | 80 |
| | 10 | 0 | 0 | 5 | 60 | 50 |

The compounds of the present invention have excellent herbicidal activity to barnyardgrass as well as improved rice selectivity. As shown in Table 3b, the compounds of the present invention have excellent herbicidal activity against barnyardgrass; 90% or greater depending on the compounds at 20 g/ha. Further, they show acceptable rice safety at 80 g/ha (30% or less), which is comparable to the standard compound E.

Weed Spectrum in Paddy Field

Pots having a surface area of 500 cm² were filled with the soil in a muddy state as mentioned above. Seeds of annual weeds such as *Monochoria vaginalis* (MOOVA), *Lindernia procumbens* (LIDPR), *Rotala indica* (ROTIN), *Scirpus juncoides* (SCPJU), etc. were sown on the surface layer of soil, and then were planted tubers of perennial weeds such as *Cyperus serotinus* (CYPSE) and *Sagittaria pygmaea* (SAGPY) in a depth of 1 cm, and *Eleocharis kuroguwai*

(ELOKU) and *Sagittaria trifolia* (SAGTR) in a depth of 4 cm. After 5 days, the chemicals were formulated as mentioned above and applied by dropping to the water surface of the pots. The test plants were observed for two weeks after the treatment and the results are given in the following Table 4.

TABLE 4

Weed spectrum of the compounds of the present invention in a paddy condition

| Compound | Rate (g/ha) | Annual weeds | | | | Perennial weeds | | | |
|---|---|---|---|---|---|---|---|---|---|
| | | MOOVA | LIDPR | ROTIN | SCPjU | CYPSE | SAGPY | ELOKU | SAGTR |
| Com. 2 | 20 | 100 | 100 | 100 | 100 | 100 | 95 | 95 | 90 |
| Com. 4 | 20 | 100 | 100 | 100 | 100 | 100 | 90 | 95 | 85 |

From the results of Table 4, the compounds of the present invention show high activities on various annual and perennial weeds in addition to barnyardgrass.

Consequently, the compounds of the present invention, novel herbicidal molecules in paddy conditions, effectively control the annual and perennial weeds including barnyardgrass by pre- and post-emergence treatment and provide a high level of safety to transplanted and direct-seeded rice. Therefore, they are expected to be used for such purposes.

What is claimed is:

1. A pyridine sulfonyl urea compound of the following formula (1):

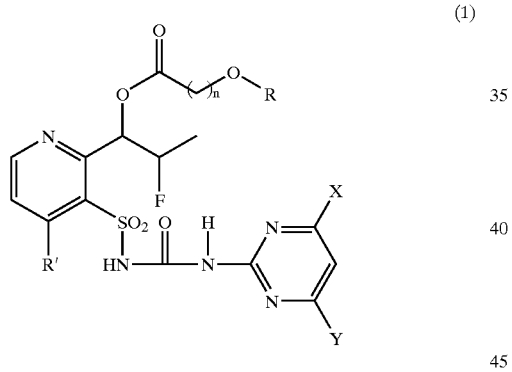

in which n denotes an integer of from 1 to 3,

R represents H or $C_1$–$C_4$-alkyl,

R' represents H, $C_1$–$C_4$-alkyl, $C_1$–$C_3$-haloalkyl, halogen, or $C_1$–$C_2$-alkoxy, and X and Y independently of one another represent $C_1$–$C_2$-alkyl, $C_1$–$C_2$-alkoxy, $C_1$–$C_2$-haloalkoxy, or halogen, salts or stereochemical isomers thereof.

2. The compound of claim 1 wherein n denotes an integer of 1 or 2, R represents H or methyl, R' represents H, Cl, Br or methyl, and X and Y each represents methoxy.

3. The compound of claim 1 wherein n denotes an integer of 1 or 2, R represents methyl, R' represents H, Cl, Br, or methyl, and X and Y each represents methoxy.

4. The compound of claim 1 selected from the group consisting of:

N-[(4,6-dimethoxypyrimidin-2-yl)aminocarbonyl]-2-(2-fluoro-1-methoxyactetoxy-n-propyl)pyridine-3-sulfonamide;

N-[(4,6-dimethoxypyrimidin-2-yl)aminocarbonyl]-2-(2-fluoro-1-hydroxyactetoxy-n-propyl)pyridine3-sulfonamide;

N-[(4,6-dimethoxypyrimidin-2-yl)aminocarbonyl]-2-(2-fluoro-1-(3-hydroxypropion)oxy-n-propyl)pyridine-3-sulfonamide;

N-[(4,6-dimethoxypyrimidin-2-yl)aminocarbonyl]-2-(2-fluoro-1-(3-methoxypropion)oxy-n-propyl)pyridine-3-sulfonamide;

N-[(4,6-dimethoxypyrimidin-2-yl)aminocarbonyl]-4-methyl-2-(2-fluoro-1-(3-hydroxypropion)oxy-n-propyl)pyridine-3-sulfonamide;

N-[(4,6-dimethoxypyrimidin-2-yl)aminocarbonyl]-4-chloro-2-(2-fluoro-1-(3-hydroxypropion)oxy-n-propyl)pyridine-3-sulfonamide; and N-[(4,6-dimethoxypyrimidin-2-yl)aminocarbonyl]-4-bromo-2-(2-fluoro-1-(3-hydroxypropion)oxy-n-propyl)pyridine-3-sulfonamide.

5. The compound of claim 1 which is present in the stereoisomeric form of erythro.

6. A process for preparing the compound of formula (1) as defined in claim 1 characterized in that a compound of the following formula (6)

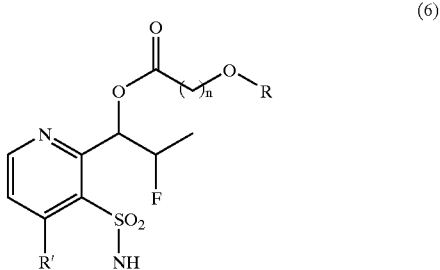

in which n denotes an integer of from 1 to 3,

R represents H or $C_1$–$C_4$-alkyl, and

R' represents H, $C_1$–$C_4$-alkyl, $C_1$–$C_3$-haloalkyl, halogen, or $C_1$–$C_2$-alkoxy, is reacted in a solvent optionally in the presence of a base with a compound of the following formula (7):

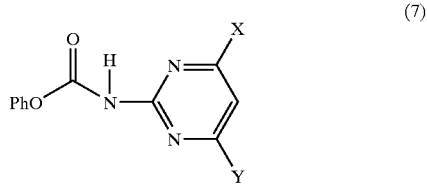

in which X and Y are defined each independently of one another represent $C_1$–$C_2$-alkyl, $C_1$–$C_2$-alkoxy, $C_1$–$C_2$-haloalkoxy, or halogen.

7. The process of claim 6 wherein the base is triethylamine, hexamethylenetetraamine, pyridine, 1,8-diazabicyclo[5,4,0]undec-7-ene (DBU) or 1,4-diazabicyclo[2,2,2]octane (DABCO).

8. A herbicidal composition for controlling weeds which comprises as an active ingredient the compound of formula (1) as defined in claim 1 together with carriers.

9. The composition of claim 8 which comprises the compound of formula (1) wherein n denotes an integer of 1 or 2, R represents H or methyl, R' represents H, halogen or methyl and X and Y each represents methoxy.

10. Method for controlling weeds against rice or wheat in paddy field or upland field condition, the method comprising administration of an effective amount of a compound of formula (1) as defined in claim 1 to the rice or wheat in the paddy field or upland field condition.

* * * * *